(12) United States Patent
Hendriks

(10) Patent No.: US 6,224,559 B1
(45) Date of Patent: May 1, 2001

(54) DEVICE FOR HIGH-RESOLUTION, NONINVASIVE BLOOD PRESSURE MEASUREMENT

(75) Inventor: Frans Hendriks, Sprang-Capelle (NL)

(73) Assignee: Dräger Medizintechnik GmbH (DE)

( * ) Notice: Subject to any disclaimer, the term of this patent is extended or adjusted under 35 U.S.C. 154(b) by 0 days.

(21) Appl. No.: 09/328,249

(22) Filed: Jun. 8, 1999

(30) Foreign Application Priority Data

Nov. 27, 1998 (DE) .............................................. 198 54 825

(51) Int. Cl.$^7$ ....................................................... A61B 5/02
(52) U.S. Cl. ........................... 600/490; 600/493; 600/485
(58) Field of Search .................................... 600/481, 485, 600/490, 493–495, 500

(56) References Cited

U.S. PATENT DOCUMENTS 4,703,760   11/1987   Miyawaki et al. .
4,880,013   11/1989   Chio .

*Primary Examiner*—Max Hindenburg
*Assistant Examiner*—Ryan Carter
(74) *Attorney, Agent, or Firm*—McGlew and Tuttle, P.C.

(57) ABSTRACT

A device for the noninvasive blood pressure measurement with a cuff and with a corresponding control and evaluating circuit. The device provides improvements in terms of the signal resolution. On the one hand, the cuff (1) is connected via a pressure sensor with pressure transducer (4) to a downstream amplifier (5), which is preferably designed as an operational amplifier, and to an analog-digital converter (6) arranged directly downstream of the amplifier (5) with the computing and control unit (2). On the other hand, the computing and control unit (2) is connected to the cuff (1) via an electronically driven pressure transducer (3).

8 Claims, 1 Drawing Sheet

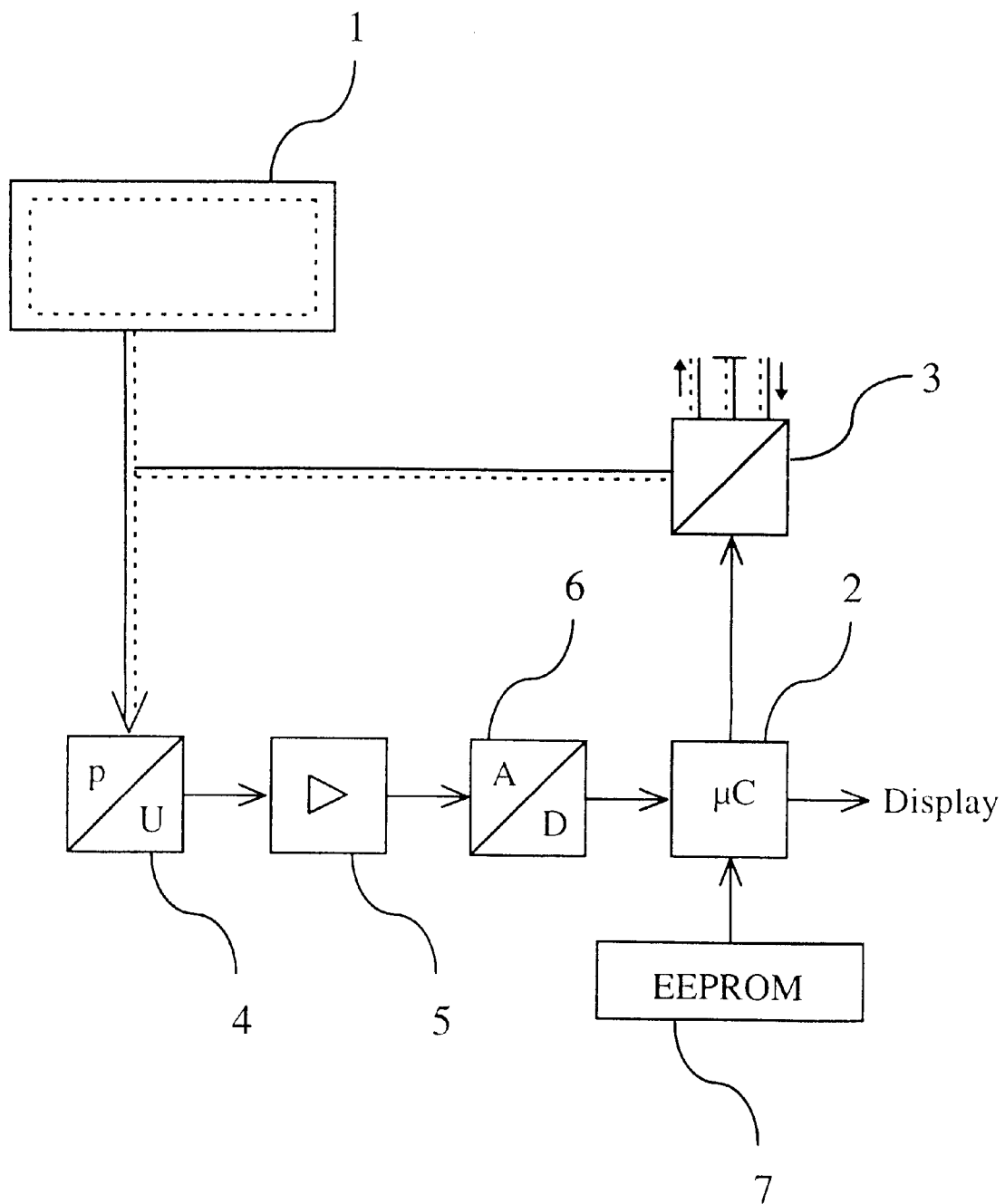

DEVICE FOR HIGH-RESOLUTION, NONINVASIVE BLOOD PRESSURE MEASUREMENT

FIELD OF THE INVENTION

The present invention pertains to a device for noninvasive blood pressure measurement, the device including a cuff and a control and evaluating circuit.

BACKGROUND OF THE INVENTION

Noninvasive blood pressure measurements are performed by means of corresponding devices and processes and have been known in many variants. For example, EP 0 029 166 B1 describes an electronic blood pressure-measuring device that has a circuit for processing the measured signals.

The prior-art processes and devices are based on the separation of a quasi static signal from a superimposed dynamic signal by means of analog electronic components in suitable evaluating circuits.

In the idealized case, the quasi static signal is a step function decreasing especially over time, which reproduces the currently present pressure preset in the inflatable cuff. The medical measured value that is actually of interest can be determined only from the superimposed dynamic signal.

The separation of the two signals is usually performed in prior-art measuring and evaluating devices via analog filter elements, which have an operational amplifier connected as a high-pass filter with a downstream analog-digital converter.

One essential drawback of the prior-art devices is the dead times of up to 150 msec occurring during measurement in the case of a reduction of the pressure in the cuff by one pressure stage each.

SUMMARY AND OBJECTS OF THE INVENTION

Correspondingly, the primary object of the present invention is to provide an improved device for noninvasive blood pressure measurement, which has a higher time resolution and measuring sensitivity with respect to the evaluation of the measured values.

According to the invention, a device is provided for noninvasive blood pressure measurement. The device includes a cuff and a control and evaluating circuit. The cuff is connected, on the one hand, to a downstream amplifier via a pressure sensor with a pressure transducer. An analog-digital converter is arranged directly downstream of the amplifier with the computing and control unit. On the other hand, the computing and control unit is connected to the cuff via an electronically driven pressure transducer.

One essential advantage of the device according to the present invention is that a marked improvement is achieved in noninvasive blood pressure measurement and evaluation in medical engineering by means of available electronic components that are known per se based on the arrangement described.

The analog-digital converter may have a resolution of at least 16 bits and a scanning rate of at least 50 Hz.

The electrically driven pressure transducer may be designed as a pump that can be driven electronically with an associated valve that can be driven electronically. In this way, the pressure preset by the computing and control unit is set and changed in the cuff in a time-dependent manner. The cuff may be pneumatically connected to the pressure transducer.

The computing and control unit preferably has one or more microprocessors. The process steps determining the pressure control, the measurement evaluation and the output of the measured values are preferably stored in a, permanently writable memory associated with the computing and control unit. The process steps determining the pressure control and the filter process may be synchronously coupled in the computing and control unit, which has at least one microprocessor.

The various features of novelty which characterize the invention are pointed out with particularity in the claims annexed to and forming a part of this disclosure. For a better understanding of the invention, its operating advantages and specific objects attained by its uses, reference is made to the accompanying drawing and descriptive matter in which a preferred embodiment of the invention is illustrated.

BRIEF DESCRIPTION OF THE DRAWING

In the drawing:

The only FIGURE is a schematic view of the circuitry of a device according to the present invention.

DESCRIPTION OF THE PREFERRED EMBODIMENT

Referring to the drawings in particular, the only FIGURE is a schematic view of the circuitry of a device according to the present invention.

Via a pressure transducer 3 (e.g. an electrically driven pressure transducer 3), an inflatable cuff 1 (which is itself known) is set, on the one hand, to the quasi static pressure preset by the computing and control unit 2, which is, in general, at least a microprocessor. The quasi static pressure preset is, in general, a step function decreasing over time. The resulting temporary pressure of the cuff 1 is sent to a pressure transducer 4 (e.g. a sensor with a pressure transducer for sensing pressure and generating an electric output signal).

The pressure transducer 3 may be designed as a pump that can be driven electronically with an associated valve that can be driven electronically. In this way, the pressure preset by the computing and control unit 2 is set and changed in the cuff in a time-dependent manner. The cuff is, for example, pneumatically connected to the pressure transducer 3.

The electric output signals of the pressure sensor or pressure transducer 4 are amplified by means of an amplifier 5. The amplifier 5 is preferably designed as an operational amplifier and the output signals are digitized, without the insertion of additional electronic components, in an analog-digital converter 6, which has a resolution of at least 16 bits and a scanning rate of at least 50 Hz.

The signal processing proper takes place in the computing and control unit 2, which has one or more correspondingly connected microprocessors.

Both the evaluation algorithms and the process control steps are stored in a permanently writable memory 7, especially in an EEPROM (Electrically Erasable Programmable Read Only Memory). All the process steps relevant for the measurement can be changed by correspondingly changing the contents of the memory 7. These are, on the one hand, the process steps relevant for the pressure control of the cuff 1 by means of the pressure transducer 3, and, on the other hand, the process steps relevant for the separation of the quasi static signal from the superimposed dynamic signal and for the calculation of the blood pressure values, i.e., the measurement evaluation proper, and, finally, the process steps relevant for the display, storage and optionally the transmission of the medical measured values stored.

One important feature of the control and evaluating circuit of the device according to the present invention is that the analog-digital converter 6 is arranged directly downstream of the amplifier 5 designed as an operational amplifier and it has a high resolution of at least 16 bits and a high scanning rate of at least 50 Hz for the measured signal.

The superimposed dynamic signals are first separated from the quasi static signal in a mathematical filter process in the computing and control unit 2. The dynamic signals, which are the actually relevant signals, are attributed in a subsequent, further computation process to the characteristic blood pressure values (systolic/diastolic) that are ultimately of interest by means of a corresponding algorithm. These characteristic blood pressure values are finally displayed, stored and/or transmitted for further processing (indicated by the "Display" arrow in the FIGURE).

While a specific embodiment of the invention has been shown and described in detail to illustrate the application of the principles of the invention, it will be understood that the invention may be embodied otherwise without departing from such principles.

What is claimed is:

1. A device for noninvasive blood pressure measurement, comprising:

an inflatable cuff;

an electronically driven pressure transducer for setting the pressure in the cuff;

a computing and control unit connected to said cuff via said electronically driven pressure transducer;

a pressure sensor with a pressure transducer connected to said cuff;

an amplifier downstream of said pressure sensor, said cuff being connected to said downstream amplifier via said pressure sensor with said pressure transducer;

an analog-digital converter arranged directly downstream of said amplifier, said analog-digital converter being connected to said amplifier and to said computing and control unit and receiving an analog signal from said amplifier and providing a digital signal to said computing and control unit.

2. The device in accordance with claim 1, wherein said analog-digital converter has a resolution of at least 16 bits and a scanning rate of at least 50 Hz.

3. The device in accordance with claim 1, wherein said pressure transducer is designed as a pump that can be driven electronically with an associated valve that can be driven electronically, so that the pressure preset by the computing and control unit is set and changed in said cuff in a time-dependent manner.

4. The device in accordance with claim 2, wherein said pressure transducer is designed as a pump that can be driven electronically with an associated valve that can be driven electronically, so that the pressure preset by the computing and control unit is set and changed in said cuff in a time-dependent manner.

5. The device in accordance with claim 1, wherein said cuff is pneumatically connected to said electronically driven pressure transducer.

6. The device in accordance with claims 1, wherein said computing and control unit has one or more microprocessor.

7. The device in accordance with claim 1, further comprising a permanently writable memory associated with said computing and control unit, wherein process steps including determining the pressure control, the measurement evaluation and the output of the measured values are stored in said permanently writable memory.

8. The device in accordance with claim 7, wherein said process step of determining the pressure control and a filter process are synchronously coupled in said computing and control unit, which has at least one microprocessor.

* * * * *